United States Patent [19]

Dechow

[11] Patent Number: 4,837,255
[45] Date of Patent: Jun. 6, 1989

[54] PALATABLE HYPOCHOLESTEROLAEMIC GEL FORMULATION CONTAINING A PHARMACEUTICALLY ACCEPTABLE NON-DIGESTIBLE ANION EXCHANGE RESIN

[75] Inventor: Frederick J. Dechow, Summit, N.J.

[73] Assignee: Ciba-Geigy Corporation, Ardsley, N.Y.

[21] Appl. No.: 24,224

[22] Filed: Mar. 10, 1987

[51] Int. Cl.$^4$ .................... A61K 37/02; A61K 43/00
[52] U.S. Cl. .......................... 524/23; 424/439; 424/440; 424/456; 424/470; 424/485; 424/486; 424/492; 424/493; 424/497; 514/774; 514/801; 514/951; 514/974
[58] Field of Search .............. 524/23; 424/439, 440, 424/458, 456, 469, 470, 485, 486, 489, 490, 492, 493, 497; 514/774, 801, 951, 974

[56] References Cited

U.S. PATENT DOCUMENTS

| | | | |
|---|---|---|---|
| 2,581,035 | 1/1952 | Martin et al. | 167/55 |
| 2,656,298 | 10/1953 | Loewe | 167/55 |
| 3,846,541 | 11/1974 | Howard | 424/79 |
| 3,974,272 | 8/1976 | Polli et al. | 424/78 |
| 4,042,687 | 8/1977 | Gans et al. | 514/21 |
| 4,115,537 | 9/1978 | Driscoll et al. | 424/1 |
| 4,172,120 | 10/1979 | Todd et al. | 424/44 |
| 4,252,790 | 2/1981 | Higuchi et al. | 424/79 |
| 4,719,228 | 1/1988 | Rawlins | 514/456 |

OTHER PUBLICATIONS

USAN and the USP Dictionary of Drug Names, p. 76, (1986).

*Primary Examiner*—John Kight
*Assistant Examiner*—Nathan M. Nutter
*Attorney, Agent, or Firm*—Irving M. Fishman

[57] ABSTRACT

A gel formation for oral administration having improved palatability comprising an effective hypocholesterolaemic amount of a uniform gelled dispersion of
(a) between about 8 and about 20 percent by weight of a particulate, pharmaceutically acceptable, sparingly crosslinked non-digestible quaternary ammonium substituted polysytrene anion exchange resin having an average particle size below about 100 microns;
(b) between about 4 and about 16 percent by weight of a pharmaceutically acceptable gelatin;
(c) between about 0.015 and about 10 percent by weight of a natural or synthetic pharmaceutically acceptable sweetener;
(d) between about 0.05 and about 2 percent by weight of a pharmaceutically acceptable organic acidulent;
(e) between about 0.05 and about 5 percent by weight of one or more pharmaceutically acceptable flavoring or coloring agents or mixtures thereof; and
(f) the remainder water.

9 Claims, No Drawings

PALATABLE HYPOCHOLESTEROLAEMIC GEL FORMULATION CONTAINING A PHARMACEUTICALLY ACCEPTABLE NON-DIGESTIBLE ANION EXCHANGE RESIN

BACKGROUND OF THE INVENTION

Pharmaceutically acceptable particulate sparingly crosslinked non-digestible quaternary ammonium substituted polystyrene anion exchange resins, such as cholestyramine resin powder, are known hypocholesterolaemic agents. See, for example U.S. Pat. No. 3,383,281 to Wolf et al. incorporated by reference herein.

Such resins are administered orally, generally in the form of a powder which is admixed with a beverage, such as water, milk, fruit juice or other non-carbonated beverage, or with highly fluid soups or pulpy fruits with a high moisture content such as applesauce or crushed pineapple. In the intestinal tract, the indigestible resin adsorbs and combines with bile acids to form an insoluble complex which is excreted. The increased loss of bile acids due to resin administration leads to an increased oxidation of cholesterol to bile acids, a decrease in beta lipoprotein or low density lipoprotein plasma levels and a decrease in serum cholesterol levels. Although in man, the oral administration of such resins results in an increase in hepatic synthesis of cholesterol, plasma cholesterol levels fall.

Accordingly, such resins are useful in the reduction of elevated serum cholesterol in patients with hypercholesterolemia and in the relief of pruritis.

Unfortunately such resins in particulate form characteristically exhibit a chalky, gritty texture or taste in the mouth of the patient, even when combined with a beverage, soup or pulpy fruit. In some patients, this undesirable characteristic of the resin may elicit a gagging reflex. As a result, patient compliance to the self administration of the resin orally may be reduced.

It is therefore an object of the present invention to provide a pharmaceutically acceptable gelled composition containing an effective hypocholesterolaemic amount of a particulate sparingly crosslinked non-digestible quaternary ammonium substituted polystyrene anion exchange resin which possesses a high degree of palatability.

It is a further object of the present invention to provide a method treating a patient by orally administering an effective hypocholesterolaemic amount of such gelled composition.

These and other objects of the invention are apparent from the following specification disclosures.

DETAILED DESCRIPTION OF THE INVENTION

One embodiment of the present invention is a gelled palatable hypocholesterolaemic formulation for oral administration to a patient comprising an effective hypocholesterolaemic amount of a uniform gelled dispersion of (a) between about 8 and about 20 percent by weight of a particulate sparingly crosslinked non-digestible quaternary ammonium substituted polystyrene anion exchange resin having an average particle size below about 100 microns;

(b) between about 4 and about 16 percent by weight of a pharmaceutically acceptable gelatin;

(c) between about 0.015 and about 10 percent by weight of a natural or synthetic pharmaceutically acceptable sweetener;

(d) between about 0.05 and about 2 percent by weight of a pharmaceutically acceptable organic acidulent;

(e) between about 0.05 and about 5 percent by weight of one or more pharmaceutically acceptable flavoring or coloring agents or mixtures thereof; and (f) the remainder water.

The particulate resin component (a) belongs to a well known class of pharmaceutically acceptable particulate anion exchange resins useful in the reduction of cholesterol and triglyceride levels and the relief of pruritis in patients suffering from bile stasis. Such resins possess quaternary ammonium groups attached to a polystyrene containing backbone. Preferably such quaternary groups are tri-lower alkyl ammonium groups wherein the nitrogen thereof is attached to the phenyl moiety of the styryl group. The most preferred lower alkyl group is methyl. Further the resin is sparingly crosslinked, e.g. with a conventional divinyl crosslinking agent, especially divinyl benzene. The amount of crosslinker present in the final resin is generally below about 5%, preferably between about 1 and about 4%, most preferably about 2%, by weight of dry resin. The resins can be prepared, for example, as described in U.S. Pat. No. 2,591,573. The quaternary ammonium resin is in the form of a pharmaceutically acceptable salt thereof, such as the chloride, acetate, sulfate or the like. Generally, useful resins are those having a water content greater than about 65% by weight after equibration with air at 100% relative humidity at about 20° C. Most preferably, the resin employed is cholestyramine resin U.S.P. The resin should be milled such that the average particle size is less than about 100 microns. Preferably, at least about 80 percent of the resin particles have a particle size between about 20 and about 100 microns, with less than about 0.5% of the particles having a particle size greater than about 200 microns. Preferably, the amount of resin in the composition is between about 12 and about 18 percent by weight.

Component (b) consists of a pharmaceutically acceptable gelatin, such as gelatin USP, which is soluble in hot water, e.g. above about 35° C., and, in the amount employed, forms a stable elastic shape retaining colloidal solution within which the resin component is substantially uniformly dispersed upon cooling to room temperature, e.g. about 20° C. The preferred amount of gelatin employed is between about 5 to about 10 percent by weight of the formulation. The preferred gelatin is gelatin USP, type A. The gelatin component in the amounts specified also assists in masking the chalky characteristics of the resin.

The sweetener component (c) may be selected from any of a large number of well known sweetening excipients, including for example sucrose, aspartame, corn syrup, glucose, fructose, mannose, and sorbitol and mixtures thereof. The amount of sweetener component within the ranges specified, will, of course, depend in part on the nature of the sweetening agent. Preferred is aspartame in an amount between about 0.15 to about 0.75 percent by weight.

The pharmaceutically acceptable organic acidulant (d) is present in combination with the sweetner and gelatin for the purpose of further masking the unpleasant mouth feel of the active agent resin, and include, for example adipic acid, ascorbic acid, citric acid, malic acid and tartaric acid or mixtures thereof. Again the optimum amount will, in part, depend upon the particular acidulant chosen. Preferably, the amount of acidulant is between about 0.1 and about 0.5 percent by weight. The most preferred acidulant is adipic acid.

The pharmaceutically acceptable flavoring and coloring agents (e) may be selected from any of a wide variety of known agents and include FD&C colors as well as artificial and natural flavors, including lime, cherry, orange, banana, spearmint, lemon, raspberry, blueberry, vanilla, strawberry, cinnamon, peppermint and the like, as well as mixtures thereof.

Also, if desired, minor amounts, preferably between about 0.01 to about 1.0 percent of pharmaceutically acceptable preservatives, stabilizers or anti-binding agents and the like may be present in the composition. Suitable such preservatives include potassium sorbate and sodium propionate. As an anti-binding agent, to reduce the potential of constipation in some patients, methylcellulose is preferred.

The compositions of the instant invention are easily prepared by combining the ingredients with water, with heating above 35° C., while blending the mixture and subsequently cooling the resulting uniformly dispersed sol.

If desired, prior to cooling and consequent gelatinization, the dispersed liquid, containing uniformly suspended resin can be poured into individual containers or molds of desired shape and size where the liquid sol hardens to the desired elastic shape retaining colloidal solution containing the uniformly dispersed particulate resin. As an alternate embodiment, the gelatinization can be performed in trays, or the like, and unit dose forms can be obtained by, for example, cutting portions therefrom.

The unit dose may vary widely, depending on the condition treated, but is preferably between about 2 to 16 grams of active agent resin, most preferably about 4 grams of active agent resin.

The following examples are for illustrative purposes only and are not intended to limit the scope of the invention. All parts are by weight.

EXAMPLE 1

2.0 Parts by weight gelatin USP, type A is dissolved in 24.0 parts by weight water at 60° C. with stirring. After stirring the solution for 3 minutes, 4.0 parts by weight of dry cholestyramine, "Dowex 1×2" made by Dow Chemical Co., Midland, Mich. and containing about 2% of divinyl benzene crosslinking agent, which has been milled and screened to obtain an average particle size less than about 100 microns, with about 80 percent having a particle size between about 20 to about 100 microns, and 0.07 parts by weight aspartame are added to the solution with stirring at 60° C. After stirring for an additional 3 minutes, there is then added to the liquid mixture maintained at 60° C., 0.10 parts by weight adipic acid and 0.10 parts by weight of a mixture of artificial strawberry flavor and FD&C Red dissolved in ethanol. After stirring the mixture for an additional 5 minutes, the uniformly distributed suspension of resin in the resulting solution is placed in rectangular molds where, upon allowing the mixture to cool to room temperature for a period of two hours, the stable elastic shape retaining colloidal solution, or gel, containing the resin uniformly dispersed therein, is obtained.

EXAMPLE 2

A composition identical in composition components to that of Example 1 is prepared, except that 0.2 parts of methyl cellulose is added to the solution with aspartame and resin. The resulting gel is substantially identical to that of Example 1. Due to the additional presence of methyl cellulose, the incidence of possible constipation is minimized.

What is claimed is:

1. A hypocholesterolaemic gel formulation for oral administration comprising an effective hypocholesterolaemic amount of a uniform gelled dispersion of:
    (a) between about 8 and about 20 percent by weight of a particulate, sparingly crosslinked non-digestible pharmaceutically acceptable quaternary ammonium substituted polystyrene anion exchange resin having an average particle size below about 100 microns;
    (b) between about 4 and about 16 percent by weight of a water compatable pharmaceutically acceptable gelatin;
    (c) between about 0.015 and about 10 percent by weight of a natural or synthetic pharmaceutically acceptable sweetener;
    (d) between about 0.05 and about 2 percent by weight of a pharmaceutically acceptable organic acidulent;
    (e) between about 0.05 and about 5% by weight of one or more pharmaceutically acceptable flavoring or coloring agents, or mixtures thereof; and
    (f) the remainder water.

2. A formulation according to claim 1 wherein the amount of said resin in the formulation is between about 12 and about 18 percent by weight.

3. A formulation according to claim 1 wherein the resin is cholestyramine.

4. A formulation according to claim 1, wherein said gelatin is gelatin USP, type A.

5. A formulation according to claim 1, wherein the sweetening agent is aspartame and the acidulent is adipic acid.

6. A formulation according to claim 1, wherein the resin is cholestyramine, the sweetening agent is aspartame, and the acidulent is adipic acid.

7. A method of treating hypercholesterolaemia in a patient comprising orally administering to said patient in need of the same, an effective hypocholesterolaemic amount of the formulation according to claim 1.

8. A method according to claim 7, wherein the resin is cholestyramine.

9. A method according to claim 7, wherein the resin is cholestyramine, the sweetener is aspartame and the acidulent is adipic acid.

* * * * *